US010292916B2

(12) United States Patent
Chaudhary et al.

(10) Patent No.: US 10,292,916 B2
(45) Date of Patent: *May 21, 2019

(54) ANTI-ADHERENT ALCOHOL-BASED COMPOSITION

(71) Applicant: KIMBERLY-CLARK WORLDWIDE, INC., Neenah, WI (US)

(72) Inventors: Vinod Chaudhary, Appleton, WI (US); Scott W. Wenzel, Neenah, WI (US); Kathleen C. Engelbrecht, Kaukauna, WI (US); David W. Koenig, Menasha, WI (US); Amy L. Vanden Heuvel, Hortonville, WI (US); Divesh Bhatt, Marietta, GA (US); Paige N. Hollmaier (Anunson), Neenah, WI (US); Stacy A. Mundschau, Weyauwega, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/011,248

(22) Filed: Jun. 18, 2018

(65) Prior Publication Data

US 2019/0015308 A1 Jan. 17, 2019

Related U.S. Application Data

(63) Continuation of application No. 15/500,671, filed as application No. PCT/US2015/023852 on Apr. 1, 2015, now Pat. No. 10,028,899.

(60) Provisional application No. 62/031,526, filed on Jul. 31, 2014.

(51) Int. Cl.
| | |
|---|---|
| A61K 8/34 | (2006.01) |
| C09D 5/14 | (2006.01) |
| C09D 101/28 | (2006.01) |
| A61K 8/73 | (2006.01) |
| A61Q 17/00 | (2006.01) |
| A61K 8/81 | (2006.01) |
| A61K 8/02 | (2006.01) |

(52) U.S. Cl.
CPC .............. *A61K 8/34* (2013.01); *A61K 8/0208* (2013.01); *A61K 8/73* (2013.01); *A61K 8/731* (2013.01); *A61K 8/8152* (2013.01); *A61Q 17/005* (2013.01); *C09D 5/14* (2013.01); *C09D 101/28* (2013.01); *C09D 101/284* (2013.01)

(58) Field of Classification Search
CPC .................................................... A61K 33/38
See application file for complete search history.

(56) References Cited

U.S. PATENT DOCUMENTS

| | | |
|---|---|---|
| 1,680,584 A | 8/1928 | Angell |
| 3,241,898 A | 3/1966 | Propst |
| 3,338,992 A | 8/1967 | Kinney |
| 3,341,394 A | 9/1967 | Kinney |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo |
| 3,692,618 A | 9/1972 | Carduck |
| 3,802,817 A | 4/1974 | Goto |
| 3,849,241 A | 11/1974 | Butin |
| 4,007,113 A | 2/1977 | Ostreicher |
| 4,100,324 A | 7/1978 | Anderson |
| 4,144,370 A | 3/1979 | Boulton |
| 4,340,563 A | 7/1982 | Appel |
| 4,361,486 A | 11/1982 | Hou |
| 4,624,890 A | 11/1986 | Lloyd |
| 4,795,668 A | 1/1989 | Krueger |
| 5,057,361 A | 10/1991 | Sayovitz |
| 5,057,368 A | 10/1991 | Largman |
| 5,069,970 A | 12/1991 | Largman |
| 5,108,820 A | 4/1992 | Kaneko |
| 5,162,074 A | 11/1992 | Hills |
| 5,277,976 A | 1/1994 | Hogle |
| 5,284,703 A | 2/1994 | Everhart |
| 5,336,552 A | 8/1994 | Strack |
| 5,350,624 A | 9/1994 | Georger |

(Continued)

FOREIGN PATENT DOCUMENTS

| | | |
|---|---|---|
| CN | 102613214 A | 8/2012 |
| CN | 102784079 A | 11/2012 |

(Continued)

OTHER PUBLICATIONS

Katsikogianni, M. and Y.F. Missirlis, "Concise Review of Mechanisms of Bacterial Adhesion to Biomaterials and of Techniques Used in Estimating Bacteria-Material Interactions," European Cells and Materials, vol. 8, University of Patras, Patras, Greece, Dec. 2004, pp. 37-57.

(Continued)

*Primary Examiner* — San Ming R Hui
(74) *Attorney, Agent, or Firm* — Kimberly-Clark Worldwide, Inc.

(57) ABSTRACT

The present disclosure is directed to alcohol-based anti-adherent compositions that do not adhere to or attract Gram-negative and Gram-positive bacteria once it is applied to a surface and dried. The composition may include as anti-adherent agents, hydrophilic film-formers such as cellulosics, gums, acrylates, nonionic polymers, and anionic polymers. Examples of anti-adherent agents include Hydroxypropyl methylcellulose, Cellulose gum, Acacia Senegal Gum; Polyacrylate Crosspolymer-11, VP/Dimethylaminoethylmethacrylate/Polycarbamyl Polyglycol Ester; Acrylates/Vinyl Neodecanoate Crosspolymer, hydroxypropyl methylcellulose, Hydroxypropylcellulose, Methylcellulose, Propylene Glycol Alginate, Polyacrylate Crosspolymer-6, VP/Polycarbamyl Polyglycol Ester, Acrylates/Steareth-20 Methacrylate Copolymer; Acrylates Copolymer, and any combination thereof. The anti-adherent may be applied to surfaces using a vehicle such as a wipe.

20 Claims, No Drawings

(56) References Cited

U.S. PATENT DOCUMENTS

| | | |
|---|---|---|
| 5,382,400 A | 1/1995 | Pike |
| 5,466,410 A | 11/1995 | Hills |
| 5,512,186 A | 4/1996 | Wright |
| 5,593,599 A | 1/1997 | Wright |
| 5,736,058 A | 4/1998 | Wright |
| 5,742,943 A | 4/1998 | Chen |
| 5,785,179 A | 7/1998 | Buczwinski |
| 5,855,788 A | 1/1999 | Everhart |
| 5,908,707 A | 6/1999 | Cabell |
| 5,935,883 A | 8/1999 | Pike |
| 5,942,219 A | 8/1999 | Hendriks |
| 5,951,965 A | 9/1999 | Ansari |
| 5,964,351 A | 10/1999 | Zander |
| 5,989,004 A | 11/1999 | Cook |
| 6,030,331 A | 2/2000 | Zander |
| 6,110,381 A | 8/2000 | Wright |
| 6,123,996 A | 9/2000 | Larsson |
| 6,158,614 A | 12/2000 | Haines |
| 6,180,584 B1 | 1/2001 | Sawan |
| 6,200,669 B1 | 3/2001 | Marmon |
| 6,231,719 B1 | 5/2001 | Garvey |
| 6,241,898 B1 | 6/2001 | Wright |
| 6,248,880 B1 | 6/2001 | Karlson |
| 6,267,996 B1 | 7/2001 | Bombardelli |
| 6,269,969 B1 | 8/2001 | Huang |
| 6,269,970 B1 | 8/2001 | Huang |
| 6,273,359 B1 | 8/2001 | Newman |
| 6,274,041 B1 | 8/2001 | Williamson |
| 6,294,186 B1 | 9/2001 | Beerse |
| 6,306,514 B1 | 10/2001 | Weikel |
| 6,315,864 B2 | 11/2001 | Anderson |
| 6,340,663 B1 | 1/2002 | Deleo |
| 6,515,095 B1 | 2/2003 | Omura |
| 6,565,749 B1 | 5/2003 | Hou |
| 6,569,828 B1 | 5/2003 | Thomas |
| 6,630,016 B2 | 10/2003 | Koslow |
| 6,639,066 B2 | 10/2003 | Boström |
| 6,696,070 B2 | 2/2004 | Dunn |
| 6,770,204 B1 | 8/2004 | Koslow |
| 6,838,005 B2 | 1/2005 | Tepper |
| 6,916,480 B2 | 7/2005 | Anderson |
| 6,946,196 B2 | 9/2005 | Foss |
| 7,169,304 B2 | 1/2007 | Hughes |
| 7,192,601 B2 | 3/2007 | Walker |
| 7,287,650 B2 | 10/2007 | Koslow |
| 7,288,513 B2 | 10/2007 | Taylor |
| 7,384,762 B2 | 6/2008 | Drocourt |
| 7,432,234 B2 | 10/2008 | Ochomogo |
| 7,569,530 B1 | 8/2009 | Pan |
| 7,576,256 B2 | 8/2009 | Björnberg et al. |
| 7,625,844 B1 | 12/2009 | Yang |
| 7,642,395 B2 | 1/2010 | Schroeder |
| 7,795,199 B2 | 9/2010 | Molinaro |
| 7,872,051 B2 | 1/2011 | Clarke |
| 7,985,209 B2 | 7/2011 | Villanueva |
| 7,993,675 B2 | 8/2011 | Oliver |
| 8,030,226 B2 | 10/2011 | Bradley |
| 8,034,844 B2 | 10/2011 | Fox |
| 8,293,699 B2 | 10/2012 | Fütterer |
| 8,318,654 B2 | 11/2012 | Hoffman |
| 8,343,523 B2 | 1/2013 | Toreki |
| 8,481,480 B1 | 7/2013 | Lam |
| 8,506,978 B2 | 8/2013 | Soerens |
| 8,530,524 B2 | 9/2013 | Wegner |
| 8,603,771 B2 | 12/2013 | Stanley |
| 8,685,178 B2 | 4/2014 | Do |
| 8,771,661 B2 | 7/2014 | MacDonald |
| 8,871,722 B2 | 10/2014 | Harding |
| 9,006,163 B2 | 4/2015 | Hourigan |
| 9,969,885 B2 | 5/2018 | Engelbrecht |
| 10,028,899 B2 | 7/2018 | Chaudhary |
| 2001/0040136 A1 | 11/2001 | Wei |
| 2001/0046525 A1 | 11/2001 | Bombardelli |
| 2002/0050016 A1 | 5/2002 | Willman |
| 2002/0189998 A1 | 12/2002 | Haase |
| 2003/0008791 A1 | 1/2003 | Chiang |
| 2003/0069317 A1 | 4/2003 | Seitz |
| 2003/0091540 A1 | 5/2003 | Ahmad |
| 2004/0009141 A1 | 1/2004 | Koenig |
| 2004/0024374 A1 | 2/2004 | Hjorth |
| 2005/0130870 A1 | 6/2005 | Ochomogo |
| 2005/0137540 A1 | 6/2005 | Villanueva |
| 2005/0182021 A1 | 8/2005 | Nichols |
| 2005/0242041 A1 | 11/2005 | Cumberland |
| 2005/0244480 A1 | 11/2005 | Koenig |
| 2005/0271595 A1 | 12/2005 | Brown |
| 2006/0008621 A1 | 1/2006 | Gusky |
| 2006/0134239 A1 | 6/2006 | Weide |
| 2006/0140899 A1 | 6/2006 | Koenig |
| 2006/0193789 A1 | 8/2006 | Tamarkin |
| 2006/0204466 A1 | 9/2006 | Littau |
| 2006/0205619 A1 | 9/2006 | Mayhall |
| 2006/0292086 A1 | 12/2006 | Curtis |
| 2007/0020649 A1 | 1/2007 | Tseng |
| 2007/0141934 A1 | 6/2007 | Sayre |
| 2007/0207104 A1 | 9/2007 | Borish |
| 2007/0237800 A1 | 10/2007 | Lahann |
| 2007/0253926 A1 | 11/2007 | Tadrowski |
| 2007/0286894 A1 | 12/2007 | Marsh |
| 2008/0102053 A1 | 5/2008 | Childers |
| 2008/0275113 A1 | 11/2008 | Huetter |
| 2008/0293613 A1 | 11/2008 | Johnson |
| 2008/0293826 A1 | 11/2008 | Rose |
| 2008/0312118 A1 | 12/2008 | Fütterer |
| 2009/0004122 A1 | 1/2009 | Modak |
| 2009/0082472 A1 | 3/2009 | Peters |
| 2009/0087465 A1 | 4/2009 | Doney |
| 2009/0155325 A1 | 6/2009 | Wenzel |
| 2009/0155327 A1 | 6/2009 | Martin |
| 2009/0191248 A1 | 7/2009 | Hoffman |
| 2009/0226498 A1 | 9/2009 | Flugge-Berendes |
| 2010/0135916 A1 | 6/2010 | Courel |
| 2010/0297029 A1 | 11/2010 | Biering |
| 2011/0009309 A1 | 1/2011 | Mertens |
| 2011/0081528 A1 | 4/2011 | Shannon |
| 2011/0091393 A1 | 4/2011 | Simmonds |
| 2011/0293681 A1 | 12/2011 | Berlin |
| 2012/0046362 A1 | 2/2012 | Kawahara |
| 2012/0121459 A1 | 5/2012 | Edgington |
| 2012/0164206 A1 | 6/2012 | Soerens |
| 2012/0207805 A1 | 8/2012 | Colman et al. |
| 2012/0294911 A1 | 11/2012 | Redmond |
| 2013/0037048 A1 | 2/2013 | Edgington |
| 2013/0079733 A1 | 3/2013 | Burt et al. |
| 2013/0209576 A1 | 8/2013 | Brumeister |
| 2013/0274110 A1 | 10/2013 | Westbye |
| 2013/0287724 A1 | 10/2013 | Hoffman |
| 2014/0014584 A1 | 1/2014 | Cone |
| 2014/0147402 A1 | 5/2014 | Klug |
| 2014/0205546 A1 | 7/2014 | Macoviak |
| 2014/0275255 A1 | 9/2014 | Pedersen |
| 2015/0010490 A1 | 1/2015 | Kim |
| 2015/0059795 A1 | 3/2015 | Vatter |
| 2015/0290102 A1 | 10/2015 | Cozean |
| 2017/0208798 A1 | 7/2017 | Chaudhary |
| 2017/0210900 A1 | 7/2017 | Engelbrecht |
| 2017/0224596 A1 | 8/2017 | Chaudhary |
| 2017/0303535 A1 | 10/2017 | Engelbrecht |
| 2017/0367350 A1 | 12/2017 | Koenig |
| 2018/0098536 A1 | 4/2018 | Koenig |

FOREIGN PATENT DOCUMENTS

| | | |
|---|---|---|
| CN | 103387894 A | 11/2013 |
| CN | 103830226 A | 6/2014 |
| CN | 103845244 A | 6/2014 |
| CN | 103865692 A | 6/2014 |
| CN | 104013682 A | 9/2014 |
| EP | 1046390 A1 | 10/2000 |
| JP | 63007785 A2 | 1/1988 |
| JP | 10218940 A | 8/1998 |
| JP | 2000110099 A2 | 4/2000 |
| JP | 3965006 B2 | 8/2007 |

(56) References Cited

FOREIGN PATENT DOCUMENTS

| WO | WO9400016 A1 | 1/1994 |
| WO | WO0128340 A2 | 4/2001 |
| WO | WO0132132 A2 | 5/2001 |
| WO | WO03066192 A1 | 8/2003 |
| WO | WO03092382 A1 | 11/2003 |
| WO | WO04062703 A1 | 7/2004 |
| WO | WO06085975 A2 | 8/2006 |
| WO | WO09065023 A1 | 5/2009 |
| WO | WO10056685 A2 | 5/2010 |
| WO | WO11083401 A2 | 7/2011 |
| WO | WO13016029 A1 | 1/2013 |
| WO | WO13052545 A1 | 4/2013 |
| WO | WO13066403 A1 | 5/2013 |
| WO | WO14032696 A1 | 3/2014 |
| WO | WO14113269 A1 | 7/2014 |
| WO | WO14139904 A1 | 9/2014 |
| WO | WO15166075 A1 | 11/2015 |
| WO | WO16018473 A1 | 2/2016 |
| WO | WO16018474 A1 | 2/2016 |
| WO | WO16018475 A1 | 2/2016 |
| WO | WO16018476 A1 | 2/2016 |

OTHER PUBLICATIONS

Hwang et al (Resveratrol antibacterial activity against *Escherichia coli* is mediated by Z-ring formation inhibition via suppression of FtsZ expression. Scientific Reports vol. 5, Article number: 10029 (2015) (Year: 2015).

Al-Waili et al (Honey and microbial infections: a review supporting the use of honey for microbial control. J Med Food. Oct. 2011; 14 (10):1079-96) (Year: 2011).

ANTI-ADHERENT ALCOHOL-BASED COMPOSITION

TECHNICAL FIELD

The present disclosure generally relates to anti-adherent, alcohol-based compositions which are effective in killing microbes on biotic and abiotic surfaces. Once the composition of the present disclosure is applied to a surface and dried, the remaining film does not attract or allow the attachment of microbes, thus minimizing the number of microbes on the surface and leaving the surface less apt to harbor microbes.

BACKGROUND OF THE DISCLOSURE

The notion of so called "germs" and germ transmission is well known by consumers. One of the best and easiest ways of preventing germ or disease transmission is by routinely washing surfaces that can carry microbes, such as the skin or hard surfaces. However, with the inconvenience or impracticality of washing under certain circumstances, such as traveling conditions or time constraints, manufacturers have introduced a plethora of antimicrobial compositions that can sanitize surfaces. For instance, there are many gel or spray hand sanitizing compositions on the market today, many of which are alcohol-based. These compositions are very effective at killing Gram-negative and Gram-positive bacteria (e.g. *Escherichia coli* and *Staphylococcus aureus*).

Although alcohol-based antimicrobial compositions are effective at the time of application, once the alcohol flashes off, some of the remaining ingredients left on the treated surface can attract and adhere to microbes. Depending on the circumstance, this can result in a seemingly "sanitized" surface which can eventually harbor more microbes than before the sanitization took place. Therefore, a person that sanitizes his or her hands with a gel antimicrobial composition could have more microbes adhere to their hands than a person that washed their hands with soap and water and completely dried them with a clean towel.

The present disclosure generally relates to alcohol-based compositions that are effective in killing Gram-positive and Gram-negative microorganisms (e.g. *E. coli* and *S. aureus*) without leaving a film behind that attracts or adheres to such microorganisms. Desirably, the antimicrobial composition is suitable for use on skin without causing undue dryness or irritation.

SUMMARY OF THE DISCLOSURE

In one aspect of the disclosure there is an anti-adherent composition for use on surfaces. The composition comprises 40% to 90% (by weight of composition) of a short-chain alcohol; and an anti-adherent agent selected from the group consisting of Hydroxypropyl methylcellulose, Cellulose gum, Acacia Senegal Gum; Polyacrylate Crosspolymer-11; VP/Dimethylaminoethylmethacrylate/Polycarbamyl Polyglycol Ester; VP/Polycarbamyl Polyglycol Ester; Acrylates/Steareth-20 Methacrylate Copolymer a mixture of Acrylates Copolymer and VP/Polycarbamyl Polyglycol Ester, Acrylates/Vinyl Neodecanoate Crosspolymer, hydroxypropyl cellulose, methylcellulose, Propylene Glycol Alginate, Polyacrylate Crosspolymer-6 and glycerin; and combinations thereof.

In another aspect of the disclosure there is an anti-adherent composition for use on surfaces. The composition comprises 40% to 90% (by weight of composition) of a short-chain alcohol; 0.01% to 20% (by weight of composition) of an anti-adherent agent; glycerin; and a hydrophilic carrier. The composition reduces the adherence of *E. coli* and *S. aureus* on the surfaces by at least 0.5 LOG according to a High Throughput Anti-adherence Test or the Viable Count Anti-Adherence Test Method.

In yet another aspect of the disclosure there is a wipe made with a nonwoven substrate and an anti-adherent composition. The composition comprises 40% to 90% (by weight of composition) of a short-chain alcohol; 0.01% to 20% (by weight of composition) of an anti-adherent agent; and a hydrophilic carrier; wherein the composition reduces the adherence of *E. coli* and *S. aureus* on the surfaces by at least 0.5 LOG according to the High Throughput Anti-adherence Test Method or the Viable Count Anti-Adherence Test Method.

DETAILED DESCRIPTION OF THE DISCLOSURE

The present disclosure is directed to an alcohol-based anti-adherent composition containing an anti-adherent and a short-chain alcohol. The composition is at least 40% alcohol by weight of the composition, and may be applied to a surface in the form of a liquid, gel, or foam. In addition, the composition may be applied to a surface using a vehicle such as a wipe.

The anti-adherent compositions may be used on biotic surfaces such as skin; or abiotic surfaces such as food prep surfaces; hospital and clinic surfaces; household surfaces; automotive, train, ship and aircraft surfaces; and the like; as long as the surface is compatible with the ingredients of the composition.

According to the High Throughput Anti-adherence Test Method or the Viable Count Anti-Adherence Test Method, infra, the anti-adherent compositions reduce adherence to Gram-negative and Gram-positive bacteria by at least 0.5 LOG, or by at least 0.9 LOG, or by at least 1 LOG.

Anti-Adherent Agents

The anti-adherent agents suitable for use in the compositions may include but not be limited to acrylates, acrylate derivatives, polysaccharides, urethanes, urethane derivatives, vinyl derivative, and silicone polyethers.

Suitable polysaccharides may include but not be limited to cellulosics and gums. Suitable nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. No. 6,123,996 to Larsson, et al.; U.S. Pat. No. 6,248,880 to Karlson; and U.S. Pat. No. 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as methyl cellulose and ethyl cellulose; hydroxypropyl cellulose, hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose, and hydroxyethyl hydroxypropyl hydroxybutyl cellulose; alkyl hydroxyalkyl cellulose ethers, such as methyl hydroxyethyl cellulose, ethyl hydroxyethyl cellulose, ethyl hydroxypropyl cellulose, methyl ethyl hydroxyethyl cellulose, and methyl ethyl hydroxypropyl cellulose; and so forth. Particularly suitable nonionic cellulosic ethers for use in the present invention are hydroxypropyl methylcellulose, cellulose gum, and methylcellulose.

Specific examples of suitable nonionic cellulose ethers for use as the nonionic polymer of the present invention includes hydroxypropyl methylcellulose, hydroxypropyl cellulose, and methylcellulose.

A specific example of a suitable nonionic cellulose ether for use as the nonionic polymer of the present invention includes hydroxypropyl methylcellulose (BENECEL E-15 [average molecular weight 15,000 Daltons] available from Ashland, BENECEL K100LV [average molecular weight 26,000 Daltons], HPMC [average molecular weight 86,000 Daltons] from Sigma Aldrich). The hydroxypropyl methylcellulose may have a molecular weight of about 1,000 Daltons to about 500,000 Daltons, or 10,000 Daltons to 100,000 Daltons, or about 10,000 Daltons to about 40,000 Daltons.

A specific example of a suitable nonionic cellulose ether for use as the nonionic polymer of the present invention includes hydroxyethylcellulose (NATROSOL 250LR [average molecular weight 90,000 Daltons] available from Ashland). The hydroxyethylcellulose may have a molecular weight of about molecular weight of about 1,000 Daltons to about 500,000 Daltons, or about 10,000 Daltons to about 100,000 Daltons, or about 75,000 Daltons to about 350,000 Daltons.

A specific example of a suitable nonionic cellulose ether for use as the nonionic polymer of the present invention includes hydroxypropyl cellulose (KLUCEL ECS [average molecular weight 80,000 Daltons] from Ashland). The ydroxypropyl cellulose may have a molecular weight of about 1,000 Daltons to about 500,000 Daltons, or about 10,000 Daltons to about 100,000 Daltons, or about 60,000 Daltons to about 100,000 Daltons.

A specific example of a suitable nonionic cellulose ether for use as the nonionic polymer of the present invention includes methylcellulose (BENECEL A4C [average molecular weight 41,000 Daltons] available from Ashland). The methylcellulose may have a molecular weight of about 1,000 Daltons to about 500,000 Daltons, or 10,000 Daltons to about 100,000 Daltons, or about 20,000 Daltons to about 50,000 Daltons.

Gums are also suitable materials for use as the anti-adherent agent. The materials in this group are generally plant-derived materials which belong to the chemical class of carbohydrates. Although chemically diverse, the unique ability of gums to swell in the presence of water and to increase the viscosity of aqueous preparations accounts for this special class. The viscosity developed by hydrophilic colloids depends on their molecular weight and the presence of various cations which may neutralize some acid functions of these carbohydrate molecules or cause some cross linking. In cosmetics, gums and the like are used to impart viscosity to all types of products. They act as suspending or gelling agents and emulsion stabilizers. Some of these gums have unique textural qualities which make them useful in water-based lubricants. Suitable gums for use in the present invention may include but not be limited to Acacia Catechu Gum, Acacia Farnesiana Gum, Acacia Senegal Gum, Acacia Seyal Gum, Acacia Seyal Gum Octenylsuccinate, Agar, Algin, Alginic Acid, Ammonium Alginate, Amylopectin, Ascorbyl Methylsilanol Pectinate, Astragalus Gummifer Gum, Boswellia Serrata Gum, Caesalpinia Spinosa Gum, Calcium Alginate, Calcium Carboxymethyl Cellulose, Calcium Carrageenan, Carboxybutyl Chitosan, Carboxymethyl Cellulose Acetate Butyrate, Carboxymethyl Chitin, Carboxymethyl Dextran, Carboxymethyl Hydroxyethylcellulose, Carboxymethyl Hydroxypropyl Guar, Carrageenan, Cassia Gum, Cellulose Gum, Ceratonia Siliqua (Carob) Gum, Cyamopsis Tetragonoloba (Guar) Gum, Dehydroxanthan Gum, Dextran, Dextran Sulfate, Dextrin, Dextrin Behenate, Gelatin, Gelatin Crosspolymer, Gellan Gum, Ghatti Gum, Glyceryl Alginate, Glyceryl Starch, Guar Hydroxypropyltrimonium Chloride, Hydrolyzed Caesalpinia Spinosa Gum, Hydrolyzed Carrageenan, Hydrolyzed Cellulose Gum, Hydrolyzed Ceratonia Siliqua Gum Extract, Galactoarabinan, Hydrolyzed Furcellaran, Hydrolyzed Gelatin, Hydrolyzed Guar, Hydrolyzed Pectin, Hydrolyzed Rhizobian Gum, Hydrolyzed Sclerotium Gum, Hydroxybutyl Methylcellulose, Hydroxyethylcellulose, Hydroxyethyl Ethylcellulose, Hydroxypropylcellulose, Hydroxypropylcellulose, Hydroxypropyl Chitosan, Hydroxypropyl Methylcellulose, Hydroxypropyl Methylcellulose Acetate/Succinate, Hydroxypropyl Methylcellulose Stearoxy Ether, Hydroxypropyl Oxidized Starch, Hydroxypropyl Starch, Hydroxypropyl Xanthan Gum, Locust Bean Hydroxypropyltrimonium Chloride, Magnesium Alginate, Maltodextrin, Methylamido Cellulose Gum, Methylcellulose, Methyl Hydroxyethylcellulose, Methylsilanol Carboxymethyl Theophylline Alginate, Natto Gum, Nonoxynyl Hydroxyethylcellulose, Olibanum, Pectin, Pistacia Lentiscus (Mastic) Gum, Potassium Alginate, Potassium Carrageenan, Potassium, Propylene Glycol Alginate, Prunus Persica (Peach) Gum, Rhizobian Gum, Sclerotium Gum, Sodium Algin Sulfate, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Polyacrylate Starch, Sodium Stearoxy PG-Hydroxyethylcellulose Sulfonate, Sodium/TEA-Undecylenoyl Alginate, Sodium/TEA-Undecylenoyl Carrageenan, Sterculia Urens Gum, Styrax Benzoin Gum, Tamarindus Indica Seed Gum, TEA-Alginate, Undecylenoyl Xanthan Gum, Welan Gum, Xanthan Gum. Specific examples of suitable gums for use in the present invention Xanthan gum (Ticaxan Xanthan Powder available from TIC), Acacia sennegal gum (Gum Arabic available from TIC), Cellulose Gum (Sigma-Aldrich) and propylene glycol alginate (available from FMC Biopolymer). Specific examples of suitable gums include but may not be limited to Cellulose gum, Acacia Senegal Gum, and Propylene Glycol Alginate.

Another suitable class of anti-adherent agents may include polystyrene sulfonates, commonly used within the cosmetic industry as film forming polymers, emulsion stabilizers and thickeners. The addition of sulfonic acid or a sulfonate function group substantially improves to water solubility of the polystyrene backbone, making it most versatile for personal care products. A particularly example is sodium polystyrene sulfonate, commercially available as Flexan II (AkzoNobel Global Personal Care).

Still another suitable example of anti-adherent agents may include acrylates and acrylate derivatives. Suitable examples include but not be limited to Polyacrylate Crosspolymer-11, VP/Dimethylaminoethylmethacrylate/Polycarbamyl Polyglycol Ester Acrylates/Steareth-20 Methacrylate Copolymer, Acrylates/Vinyl Neodecanoate Crosspolymer, and Polyacrylate Crosspolymer-6.

Another class of anti-adherent agents is polyesters, which are manufactured by polymerizing organic acids and alcohols. Of particular interest are polyesters that are water soluble or dispersible.

Another class of anti-adherent agents is Polyimides. Polyimide-1 is a terpolymer that is made by reacting poly(isobutylene-alt-maleic anhydride) with dimethylaminopropylamine and methoxy-PEG/PPG-31/9-2-propylamine in a mixture of ethanol and Water (q.v.). The resulting polymer contains both imide, ester, and acid functionality and is used in skin and hair care preparations as a film forming agent.

Another class of anti-adherent agents is Polyquaternium compounds. Polyquaterniums have been used in cosmetic industry for a long time and are known for their substantivity to hair and skin.

Another class of anti-adherent agents is copolymers of PEG, PPG or combination thereof. Specifically, Poloxamers are nonionic triblock copolymers composed of a central hydrophobic chain of polyoxypropylene (poly(propylene oxide)) flanked by two hydrophilic chains of polyoxyethylene (poly(ethylene oxide)) fall under this category. Because the lengths of the polymer blocks can be customized, many different poloxamers exist that have slightly different properties.

Another suitable anti-adherent agent may include a modified silicone having a polyether moiety. As used herein, the term "silicone" generally refers to a broad family of synthetic polymers that have a repeating silicon-oxygen backbone, including, but not limited to, polydimethylsiloxane and polysiloxanes having hydrogen-bonding functional groups selected from the group consisting of amino, carboxyl, hydroxyl, ether, polyether, aldehyde, ketone, amide, ester, and thiol groups.

Generally, any silicone may be used so long as it has a polyether moiety. Examples of polyoxyethylene derivatized dimethicones suitable for use in the compositions of the present disclosure include SILSOFT dimethicones, available from Momentive (Wilton, Conn.), such as SILSOFTSILSOFT 805 (INCI designation: PEG-8 dimethicone; molecular weight: about 10,000); SILSOFT 810 (INCI designation: PEG-8 dimethicone; molecular weight: about 1, 700), SILSOFT 840 (INCI designation: PEG-8 dimethicone; molecular weight: about 4,000), SILSOFT 870 (INCI designation: PEG-12 dimethicone; molecular weight: about 2, 100), SF1288 (INCI designation: PEG-12 dimethicone); SILSOFT 875 (INCI designation: PEG-12 dimethicone); SILSOFT 880 (INCI designation: PEG-12 dimethicone; molecular weight: about 5,000); SILSOFT 895 (INCI designation: PEG-17 dimethicone; molecular weight: about 5,000), SF1388 (INCI designation: bis-PEG-20 dimethicone). The SF1488, SILSOFT 810, SILSOFT 870, and SF1388 are linear polyoxyethylene derivatized dimethicones, while the SILSOFT 805, SILSOFT 840, SF1288, SILSOFT 875, SILSOFT 880, and SILSOFT 895 are pendant polyoxyethylene derivatized dimethicones.

The polyoxyethylene derivatized dimethicone may also include PEG derivatized dimethicones that have additional moieties added to the polymer, including bis-PEG-15 methyl ether dimethicone, dimethicone PEG-15 acetate, dimethicone PEG-8 benzoate, dimethicone PEG-7 lactate, dimethicone PEG-7 octyldodecyl citrate, dimethicone PEG-7 olivate, dimethicone PEG-8 olivate, dimethicone PEG-7 phosphate, dimethicone PEG-8 phosphate, dimethicone PEG-10 phosphate, dimethicone PEG-7 phthalate, dimethicone PEG-8 phthalate, dimethicone PEG-8 polyacrylate, dimethicone PEG-7 succinate, dimethicone PEG-8 succinate, dimethicone PEG-7 sulfate, dimethicone PEG-7 undecylenate, lauryl dimethicone PEG-10 phosphate, PEG-9 methyl ether dimethicone, PEG-10 methyl ether dimethicone, PEG-11 methyl ether dimethicone, PEG-32 methyl ether dimethicone, PEG-12 methyl ether lauroxy PEG-5 amidopropyl dimethicone, and combinations thereof.

The dimethicone derivative may also be a polyoxyethylene/polyoxypropylene derivatized dimethicone. As used herein, the term "polyoxyethylene/polyoxypropylene derivatized dimethicone" is meant to include dimethicone polymers comprising a substituted or unsubstituted polyoxyethylene/polyoxypropylene (PEG/PPG) functional group and methicone polymers comprising a substituted or unsubstituted PEG/PPG functional group. Like discussed above with regard to the polyoxyethylene derivatized dimethicones and the polyoxypropylene derivatized dimethicones, the polyoxyethylene/polyoxypropylene derivatized dimethicone may be either pendant or linear. Pendant and linear polyoxyethylene/polyoxypropylene derivatized dimethicones have the same general structures as set forth above for pendant and linear polyoxyethylene derivatized dimethicones, respectively, except R, is a substituted or unsubstituted polyethylene glycol/polypropylene glycol functional group.

Examples of polyoxyethylene/polyoxypropylene derivatized dimethicones suitable for use in the compositions of the present disclosure include SILSOFT dimethicones, available from Momentive (Wilton, Conn.), such as SILSOFT 430 (INCI designation: PEG-20/PPG-23 dimethicone; molecular weight: about 29,000), SF1188A (INCI designation: PEG/PPG 20-15 dimethicone), SILSOFT 440 (INCI designation: PEG-20/PPG-23 dimethicone; molecular weight: about 20,000), and SILSOFT 475 (INCI designation: PEG-23/PPG-6 dimethicone; molecular weight: about 19,000). SILSOFT 430, SF1188A, SILSOFT 440, and SILSOFT 475 are all pendant polyoxyethylene/polyoxypropylene derivatized dimethicones.

Other examples of suitable polyoxyethylene/polyoxypropylene derivatized dimethicones include PEG-3/PPG-10 dimethicone, PEG-4/PPG-12 dimethicone, PEG-6/PPG-11 dimethicone, PEG-8/PPG-14 dimethicone, PEG-8/PPG-26 dimethicone, PEG-10/PPG-2 dimethicone, PEG-12/PPG-16 dimethicone, PEG-12/PPG-18 dimethicone, PEG-14/PPG-4 dimethicone, PEG-15/PPG-15 dimethicone, PEG-16/PPG-2 dimethicone, PEG-16/PPG-8 dimethicone, PEG-17/PPG-18 dimethicone, PEG-18/PPG-6 dimethicone, PEG-18/PPG-18 dimethicone, PEG-19/PPG-19 dimethicone, PEG-20/PPG-6 dimethicone, PEG-20/PPG-15 dimethicone, PEG-20/PPG-20 dimethicone, PEG-20/PPG-29 dimethicone, PEG-22/PPG-23 dimethicone, PEG-22/PPG-24 dimethicone, PEG-23/PPG-6 dimethicone, PEG-25/PPG-25 dimethicone, PEG-27/PPG-27 dimethicone, PEG-30/PPG-10 dimethicone, and PPG-4-oleth-10 dimethicone (I.e., PEG-10/PPG-4 dimethicone).

The polyoxyethylene/polyoxypropylene derivatized dimethicone may also include PEG/PPG derivatized dimethicones that have additional moieties added to the polymer, including Bis-PEG-16/PPG-16 PEG-16/PPG-16 dimethicone, dimethicone PEG-20/PPG-23 benzoate, dimethicone PEG-7/PPG-4 phosphate, dimethicone PEG-12/PPG-4 phosphate, PEG-28/PPG-21 acetate dimethicone, PEG/PPG-20/22 butyl ether dimethicone, PEG/PPG-22/22 butyl ether dimethicone, PEG/PPG-23/23 butyl ether dimethicone, PEG-24/PPG-18 butyl ether dimethicone PEG-27/PPG-9 butyl ether dimethicone PEG-24/PPG-24 methyl ether glycidoxy dimethicone, PEG-10/PPG-3 oleyl ether dimethicone, and the like.

Polyoxyethylene/polyoxypropylene derivatized dimethicones are selected from the group consisting of PEG-20/PPG-23 dimethicone, PEG/PPG 20-15 dimethicone, PEG-23/PPG-6 dimethicone, and combinations thereof.

Another suitable anti-adherent agent may include a urethane or urethane derivative. Polyurethane is a polymer composed of a chain of organic units joined by carbamate or urethane moieties. Polyisocyanate is typically reacted with various polyols and other functional groups to create a broad range of physcial characteristics and film forming properties. For this invention particularly useful commercially urethane polymers are rendered hydrophilic inclusion of polyethylene glycol or other highly hydrophilic moities. Without being bound to any particular theory, the inclusion of hydrophilic moities, particularly when added in a pendant fashion to the polymer, creates a sphere of hydration in which water molecules are tightly bound to the side chains of the polymer. Unable to remove the water, bacteria are unable to effectively bind to the surface. Also, it may be advantageous to include dimethicone, vinylpyrlidone or acrylate based monomers within the polymer backbone itself to provide substantivity coating to the surface of interest. Particularly useful commercially available polyurethanes for the present invention include but are not limited to VP/Polycarbamyl Polyglycol Ester (Pecogel H-12).

Referring to Table 1, anti-adherent agents suitable for use in the present disclosure include hydrophilic film-formers such as cellulosics, gums, acrylates, nonionic polymers, and anionic polymers. Specifically, these could include but not be limited to Hydroxypropyl Methylcellulose; Hydroxypropyl Cellulose; Cellulose Gum, or Acacia Senegal Gum; a crosspolymer of 2-Acrylamido-2-methylpropane sulfonic acid, N, N-Dimethylacrylamide and acrylic acid such as Polyacrylate Crosspolymer-11; a synthetic polymer such as VP/Dimethylaminoethylmethacrylate/Polycarbamyl Polyglycol Ester, VP/Polycarbamyl Polyglycol Ester, or Acrylates/Steareth-20 Methacrylate Copolymer; and an anionic polymeric film former such as a mixture of Acrylates Copolymer and VP/Polycarbamyl Polyglycol Ester, Acrylates/Vinyl Neodecanoate Crosspolymer, Methylcellulose, Propylene Glycol Alginate, Polyacrylate Crosspolymer-6; and combinations thereof. These anti-adherent agents perform adequately and vary in anti-adherency to microbes as shown in Table 2, infra.

The anti-adherent agents can be formulated with one or more conventional and compatible carrier materials and can take multiple forms including, without limitation, aqueous solutions, gels, lotions, suspensions, sprays, foams, aerosols and the like. As the form can be water thin (i.e. spray) or take the form of a thickened solution (i.e. gel), multiple anti-adherent agents have been identified that can be used in these forms. When formulated into a thickened carrier form, multiple anti-adherents can be used. It has been found, however that some of these thickeners may adversely affect the feel of these compositions. As such, a combination of anti-adherents may be used to balance the anti-adherent activity and the feel of the composition, that is, not perceptively sticky or tacky.

One example of a thickened anti-adherent composition may include a blend of Polyacrylate Crosspolymer-11 and a modified cellulose. Examples of a modified cellulose include be Hydroxypropyl methylcellulose and Methylcellulose. The combination of the Polyacrylate Crosspolymer-11 and a modified cellulose provide a consumer-acceptable skin feel when used with an alcoholic hand-sanitizing composition, and show a larger reduction in microbe adherence than the other agents listed in Table 1. In one embodiment, the weight/weight ("w/w") ratio of Polyacrylate Crosspolymer-11 and modified cellulose may be 10:1 to 1:10, respectively. In an alternative embodiment, the w/w ratio of ingredients range between about 7.5:1 to about 1:7.5; or between about 5:1 to about 1:5; or between about 3:1 to about 1:3. In another embodiment, the weight/weight ("w/w") ratio of Polyacrylate Crosspolymer-11 and Hydroxypropyl methylcellulose or Methylcellulose may be 10:1 to 1:10, respectively. In an alternative embodiment, the w/w ratio of ingredients range between about 7.5:1 to about 1:7.5; or between about 5:1 to about 1:5; or between about 3:1 to about 1:3.

TABLE 1

Anti-Adherent Agents

| Agent | INCI | Description | Manufacturer |
|---|---|---|---|
| ACULYN 22 | Acrylates/Steareth-20 Methacrylate Copolymer | hydrophobically modified acrylate | Dow Chemicals, Midland, MI |
| ARISTOFLEX VELVET | Polyacrylate Crosspolymer-11 | polymeric sulfonic acid, neutralized | Clariant, Muttenz, Switzerland |
| CMC | Cellulose Gum | hydrophilic film former | Sigma Aldrich, St. Louis, MO |
| Gum Arabic | Acacia Senegal Gum | hydrophilic film former | Tic Gums, White March, MD |
| HPMC | Hydroxypropyl methylcellulose | hydrophobically modified cellulose | Sigma Aldrich, St. Louis, MO |
| PECOGEL GC-310 | VP/Dimethylaminoethylmethacrylate/Polycarbamyl Polyglycol Ester | synthetic polymer | Phoenix Chemicals, Sommerville, NJ |
| PECOGEL H-12 | VP/Polycarbamyl Polyglycol Ester | synthetic polymer | Phoenix Chemicals, Sommerville, NJ |
| SESAFLASH | Glycerin*, Acrylates Copolymer, VP/Polycarbamyl Polyglycol Ester, Hydrolyzed Sesame Protein PG-Propyl Methylsilanediol* | anionic polymeric emulsifier | Seppic, Paris, France |
| ACULYN 38 | Acrylates/Vinyl Neodecanoate Crosspolymer | hydrophobically modified acrylate | Dow Chemicals, Midland, MI |
| BENECEL A4C | Methylcellulose | modified cellulose | Ashland, Bridgewater, NJ |
| BENECEL E15 | Hydroxypropyl Methylcellulose | modified cellulose | Ashland, Bridgewater, NJ |
| BENECEL K100LV | Hydroxypropyl Methylcellulose | modified cellulose | Ashland, Bridgewater, NJ |
| KLUCEL ECS | Hydroxypropyl Methylcellulose | modified cellulose | Ashland, Bridgewater, NJ |
| PROTANAL ESTER BV-3750 | Propylene Glycol Alginate | polysaccharide | FMC Biopolymer, Philadelphia, PA |
| NATROSOL 250 LR | Hydroxypropylcellulose | modified cellulose | Ashland, Bridgewater, NJ |
| SEPIMAX ZEN | Polyacrylate Crosspolymer-6 | synthetic polymer | Fairfield, New Jersey |

*Carriers for the anti-adherent agents

The anti-adherent compositions of the present disclosure can suitably comprise anti-adherent agent(s) in an amount of from about 0.01% (by the total weight of the composition), to about 20% (by total weight of the composition), or from about 0.05% (by total weight of the composition) to about 15% (by total weight of the composition), or from about 0.1% (by total weight of the composition) to about 10% (by total weight of the composition).

Alcohol Carriers

The presence of an alcohol carrier in the anti-adherent compositions provides the compositions with microbiocidal properties. More particularly, the alcohol is suitably capable of killing Gram-positive, Gram-negative bacteria, fungi, parasites, and a variety of viruses. The potent activity of the alcohol against a microorganism is due to its denaturation of proteins and enzymes and cellular dehydration.

Suitable alcohols for use within the anti-adherent composition can include any water-soluble alcohol known in the art. Specific examples of suitable alcohols include, for example, methyl alcohol, ethyl alcohol, iso-propyl alcohol, n-propyl alcohol, n-butyl alcohol, t-butyl alcohol, iso-butyl alcohol, and combinations thereof.

Typically, the more concentrated the alcohol-containing composition, the more potent the antimicrobial effect. However, with respect to skin, increasing the alcohol concentration may have the deleterious effect of causing irritation. Suitably, the present disclosure describes an anti-adherent composition with an alcohol concentration of at least 40% (by total weight of the composition). More suitably, the anti-adherent composition includes from about 50% (by total weight of the composition) to about 99.98% (by total weight of the composition) alcohol, or from about 60% (by total weight of the composition) to about 80% (by total weight of the composition) and, or 62% (by total weight of the composition) to 70% (by total weight of the composition) alcohol. The alcohol(s) may be mixed with hydrophilic or hydrophobic carriers.

Additional Carriers

Non-limiting examples of suitable carrier materials include water, emollients, humectants, polyols, surfactants, esters, silicones, clays, and other pharmaceutically acceptable carrier materials.

In one embodiment, the anti-adherent compositions of the disclosure can optionally include one or more emollients, which typically serves to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

The anti-adherent compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In another embodiment, the anti-adherent compositions include one or more esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the hand sanitizing compositions or the present disclosure are listed in the *International Cosmetic Ingredient Dictionary and Handbook,* 11th Edition, CTFA, (January, 2006) ISBN-10: 1882621360, ISBN-13: 978-1882621361, and in the 2007 *Cosmetic Bench Reference, Allured* Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the anti-adherent compositions of the present disclosure include, for example, glycerin, glycerin derivatives, hyaluronic acid, hyaluronic acid derivatives, betaine, betaine derivatives amino acids, amino acid derivatives, glycosaminoglycans, glycols, polyols, sugars, sugar alcohols, hydrogenated starch hydrolysates, hydroxy acids, hydroxy acid derivatives, salts of PCA, and the like, and combinations thereof. Specific examples of suitable humectants include honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, polyethylene glycols (as listed in *the International Cosmetic Ingredient Dictionary and Handbook* such as PEG-2 through PEG 10), propanediol, xylitol, maltitol, or combinations thereof. Humectants are beneficial in that they prevent or reduce the chance that the anti-adherent film, formed after the anti-adherent agent is applied to a surface, will crack.

The anti-adherent compositions of the disclosure can desirably include one or more humectants in an amount of from about 0.01% (by total weight of the composition) to about 20% (by total weight of the composition), or from about 0.05% (by total weight of the composition) to about 10% by total weight of the composition), or from about 0.1% (by total weight of the composition) to about 5.0% (by total weight of the composition).

The anti-adherent compositions may include water. For instance, where the anti-adherent composition is a wetting composition, such as described below for use with a wet wipe, the composition will typically include water. The compositions can suitably comprise water in an amount of from about 0.1% (by total weight of the composition) to about 40% (by total weight of the composition), or from about 0.5% (by total weight of the composition) to about 39% (by total weight of the composition), or from about 1.0% (by total weight of the composition) to about 38% (by total weight of the composition).

Rheology Modifier

Optionally, one or more rheology modifiers, such as thickeners, may be added to the anti-microbial composition. Suitable rheology modifiers are compatible with the anti-adherent agent. As used herein, "compatible" refers to a compound that, when mixed with the anti-adherent agent and alcohol, does not adversely affect the anti-adherent properties of same.

A thickening system is used in the anti-adherent compositions to adjust the viscosity and stability of the compositions. Specifically, thickening systems are desirable to prevent the composition from running off of the hands or body during dispensing and use of the composition. When the sanitizing composition is used with a wipe product, a thicker formulation is desired to prevent the composition from migrating from the wipe substrate. Furthermore, by increasing the viscosity of the composition, evaporation of the alcohol within the composition is slowed, allowing for more contact time between the alcohol and microorganisms.

Generally, due to the use of alcohol as a solvent, the typical thickening system includes one or more thickeners that remain soluble in alcohol concentrations up to at least 70%. Furthermore, as noted above, the thickening system should be compatible with the compounds used in the present disclosure; that is, the thickening system, when used in combination with the anti-adherent compounds, should not precipitate out, form a coacervate or prevent a user from perceiving the conditioning benefit (or other desired benefit) to be gained from the composition. The thickening system may include a thickener, which can provide both the thickening effect desired from the thickening system and a conditioning effect to the user's skin.

Suitable thickeners include, cellulosics, gums, acrylates, starches, and various polymers. Examples could include but not be limited to hydroxethyl cellulose, potato starch, corn starch, xanthan gum, and guar gum. In some embodiments, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the composition suitably provide for compositions having a viscosity in the range of greater than 10 cP to about 30,000 cP or more. In another embodiment, the thickeners provide compositions having a viscosity of from about 100 cP to about 20,000 cP. In yet another embodiment, the thickeners provide compositions having a viscosity of from about 200 cP to about 15,000 cP.

Typically, the anti-adherent compositions of the present disclosure include the thickening system in an amount of no more than about 20% (by total weight of the composition), and more suitably, from about 0.01% (by total weight of the composition) to about 20% (by total weight of the composition). In another aspect, the thickening system is present in the anti-adherent composition in an amount of from about 0.05% (by total weight of the composition) to about 15% (by total weight of the composition), or from about 0.075% (by total weight of the composition) to about 10% (by total weight of the composition), or from about 0.1% (by total weight of the composition) to about 7.5% (by total weight of the composition).

Foaming Agents

In one embodiment, the anti-adherent composition is delivered as a foam. In accordance with the present disclosure, in order to make the composition foamable, the alcohol is combined with a foaming agent such as at least one derivatized dimethicone.

The foaming agent is capable of causing the composition to foam when the composition is combined with air using, for instance, a manual pump dispenser. Although the sanitizing composition may be dispensed from an aerosol container, an aerosol is not needed in order to cause the composition to foam. Also of particular advantage, the sanitizing composition is foamable without having to include fluorinated surfactants.

Various different derivatized dimethicone foaming agents may be used in the composition of the present disclosure. The derivatized dimethicone, for instance, may comprise a dimethicone copolyol, such as an ethoxylated dimethicone. In one embodiment, the derivatized dimethicone is linear, although branched dimethicones may be used.

The amount of foaming agent present in the foaming compositions can depend upon various factors and the desired result. In general, the foaming agent can be present in an amount from about 0.01% to about 10% by weight, such as from about 0.1% to about 5% by weight, such as from about 0.1% to about 2% by weight.

When the sanitizing composition is made foamable, it may be contained in an aerosol container. In an aerosol container, the composition is maintained under pressure sufficient to cause foam formation when dispensed.

Adjunct Ingredients

The compositions of the present disclosure may additionally include adjunct ingredients conventionally found in pharmaceutical compositions in an established fashion and at established levels. For example, the compositions may comprise additional compatible pharmaceutically active and compatible materials for combination therapy, such as anti-oxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the compositions of the present disclosure include compatible colorants, deodorants, emulsifiers, anti-foaming agents (when foam is not desired), lubricants, skin conditioning agents, skin protectants and skin benefit agents (e.g., aloe vera and tocopheryl acetate), solvents, solubilizing agents, suspending agents, wetting agents, pH adjusting ingredients (a suitable pH range of the compositions can be from about 3.5 to about 8), chelators, propellants, dyes and/or pigments, and combinations thereof.

Another component that may be suitable for addition to the anti-adherent compositions is a fragrance. Any compatible fragrance may be used. Typically, the fragrance is present in an amount from about 0% (by weight of the composition) to about 5% (by weight of the composition), and more typically from about 0.01% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the composition include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

Preservatives

The anti-microbial compositions may include various preservatives to increase shelf life. Some suitable preservatives that may be used in the present disclosure include, but are not limited to phenoxyethanol, capryl glycol, glyceryl caprylate, sorbic acid, gallic acid, KATHON CG®, which is a mixture of methylchloroisothiazolinone and methylisothiazolinone, (available from Rohm & Haas Company, Philadelphia, Pa.); DMDM hydantoin (e.g., GLYDANT, available from Lonza, Inc., Fair Lawn, N.J.); EDTA and salts thereof; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; and the like. Other suitable preservatives include those sold by Sutton Labs, Inc., Chatham, N.J., such as "GERMALL 115" (imidazolidinyl urea), "GERMALL II" (diazolidinyl urea), and "GERMALL PLUS" (diazolidinyl urea and iodopropynyl butylcarbonate).

The amount of the preservative in the anti-adherent compositions is dependent on the relative amounts of other components present within the composition. For example, in some embodiments, the preservative is present in the compositions in an amount between about 0.001% to about 5% (by total weight of the composition), in some embodiments between about 0.01 to about 3% (by total weight of the composition), and in some embodiments, between about 0.05% to about 1.0% (by total weight of the composition).

Preparation of Anti-Adherent Compositions

The anti-adherent composition of the present disclosure may be prepared by combining ingredients at room temperature and mixing.

In one embodiment, when the anti-adherent composition is to be applied to the skin of an individual, the composition includes the anti-adherent(s), alcohol(s), another hydrophilic carrier and a hydrophilic thickener. Suitable hydrophilic carriers can be, for example, water, glycerin, glycerin derivatives, glycols, water-soluble emollients, and combinations thereof. Suitable examples of alcohols include, but are not to be limited to, ethanol and isopropyl alcohol. Suitable examples of glycerin derivatives include, but are not to be limited to, PEG-7 glyceryl cocoate. Suitable glycols include, but are not to be limited to, propylene glycol, butylene glycol, pentylene glycol, ethoxydiglycol, dipropylene glycol, propanediol, and PEG-8. Suitable examples of water-soluble emollients could include, but are not to be limited to, PEG-6 Caprylic Capric Glycerides, Hydrolyzed Jojoba Esters, and PEG-10 Sunflower Glycerides.

Delivery Vehicles

The antimicrobial skin sanitizing compositions of the present disclosure may be used in combination with a product. For example, the compositions may be incorporated into or onto a substrate, such as a wipe substrate, an absorbent substrate, a fabric or cloth substrate, a tissue substrate, or the like. In one embodiment, the anti-adherent compositions may be used in combination with a wipe substrate to form a wet wipe or may be a wetting composition for use in combination with a wipe which may be dispersible. In other embodiments, the anti-adherent compositions may be incorporated into wipes such as wet wipes, hand wipes, face wipes, cosmetic wipes, cloths and the like. In yet other embodiments, the anti-adherent compositions described herein can be used in combination with numerous personal care products, such as absorbent articles or personal protective equipment. Absorbent articles of interest are diapers, training pants, adult incontinence products, feminine hygiene products, and the like; bath or facial tissue; and paper towels. Personal protective equipment articles of interest include but are not limited to masks, gowns, gloves, caps and the like.

In one embodiment, the wet wipe may comprise a nonwoven material that is wetted with an aqueous solution termed the "wetting composition," which may include or be composed entirely of the antimicrobial skin sanitizing composition disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 Grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

The disclosure will be more fully understood upon consideration of the following non-limiting Examples.

EXAMPLES

Example 1

The anti-adherent agents affect bacterial adherence to MBEC polystyrene pegs (see explanation below) in three different ways: 1) anti-adherent agents have a greater than or equal to 1 LOG reduction of bacteria to the pegs, 2) neutral agents have between 0.9 LOG reduction of bacteria to the pegs and 0.9 LOG increase of bacteria on the pegs, 3) adherent agents have a greater than or equal to 1 LOG increase of bacteria on the pegs. No agents with anti-adherent activity were found to be antimicrobial (data not shown). In this example, anti-adherent compositions of the present disclosure were tested using the High Throughput Anti-adherence Test Method or the Viable Count Anti-Adherence Test Method, infra, against Gram-positive *S. aureus*, and Gram-negative *E. coli*. Eleven of the seventy-one agents tested were found to be anti-adherent against Gram-positive *S. aureus*, and Gram-negative *E. coli*. The anti-adherent agents are shown in Table 2 below.

The pH of the anti-adherent composition is between pH 3 to 10, or about pH 4 to about 8.

Example 2

Two separate anti-adherent hand sanitizer compositions were made with the following ingredients in accordance with the procedure shown below:

TABLE 2

| Ingredients | Formulation A (%) | Formulation B (%) |
|---|---|---|
| Water | 30 | 25 |
| HPMC | 3 | 3 |
| Glycerin | 5 | 10 |
| EtOH | 62 | 62 |

Procedure: Water and Ethanol (EtOH) were added to a mixing vessel and mixing was started. Glycerin and HPMC were slowly added to this mixture under continuous stirring using an overhead stirrer. The formulation was stirred for 15 minutes to ensure complete hydration of HPMC.

Anti-adherent sanitizer compositions of the present disclosure and three commercially-available hand sanitizers were tested to determine if they were adherent to Gram-positive and/or Gram-negative bacteria. Each composition was compared to a growth control. The growth control is the measure of bacteria that attach to an untreated MBEC peg as described in detail in the test methods below. Each composition was also compared to an anti-adherent control, a composition containing 92% water, 5% glycerin, and 3% Hydroxypropyl methylcellulose. The results of the comparison tests are shown in Table 3 and Table 4 below.

In general, the three commercially available alcoholic hand sanitizers show varying degrees of anti-adherency or adherency to bacteria. Brand A is minimally adherent to both *E. coli* and *S. aureus*. Brand B is minimally adherent to *E. coli*, and minimally anti-adherent to *S. aureus*. Brand C is minimally anti-adherent to both *E. coli* and *S. aureus*. (The term "minimally adherent" is used because the effects are very small as compared to the anti-adherent control.) As can be seen, Brand B and Brand C do show some anti-adherence to *S. aureus*, and are either adherent or slightly anti-adherent to *E. coli*. In contrast, the compositions of the present disclosure show a significant degree of anti-adherence to both Gram-negative and Gram-positive bacteria.

More specifically, Table 3 shows the change in the amount of bacteria compared to the growth control present after treatment with different alcohol hand sanitizer codes. Negative numbers indicate a decrease in the amount bacteria compared to the growth control (i.e. anti-adherent to bacteria). Positive numbers indicate an increase in the amount of bacteria compared to the growth control (i.e. adherent to bacteria).

TABLE 3

| | Change compared to Growth Controls (LOG CFU/mL) | |
|---|---|---|
| Code Tested | *E. coli* ATCC 11229 | *S. aureus* ATCC 6538 |
| HPMC (10% glycerin) + EtOH | −2.6 | −3.9 |
| HPMC (5% glycerin) + EtOH | −2.2 | −3.5 |
| Brand A | 0.4 | 1.1 |
| Brand B | 1.0 | −1.0 |
| Brand C | −0.3 | −1.2 |
| Anti-adherent Control | −4.3 | −4.3 |

Table 4 shows a comparison in the efficacy against Gram-negative and Gram-positive bacteria of the proposed invention formulations versus the commercial hand sanitizer samples (as shown in LOG difference). The results are as follows:

HPMC with (10% glycerin)+EtOH is 3 LOG more anti-adherent than Brand A against *E. coli* and 5 LOG more anti-adherent against *S. aureus*

HPMC with (10% glycerin)+EtOH is 3.6 LOG more anti-adherent than Brand B against *E. coli* and 2.9 LOG more anti-adherent against *S. aureus*

HPMC with (10% glycerin)+EtOH is 2.3 LOG more anti-adherent than Brand C against *E. coli* and 2.7 LOG more anti-adherent against *S. aureus*

HPMC with (5% glycerin)+EtOH is 2.6 LOG more anti-adherent than Brand A against *E. coli* and 4.6 LOG more anti-adherent against *S. aureus*

HPMC with (5% glycerin)+EtOH is 3.2 LOG more anti-adherent than Brand B against *E. coli* and 2.5 LOG more anti-adherent against *S. aureus*

HPMC with (5% glycerin)+EtOH is 2.0 LOG more anti-adherent than Brand C against *E. coli* and 2.3 LOG more anti-adherent against *S. aureus*

TABLE 4

| | | Difference in attached bacteria when compared to commercial codes (LOG CFU/mL) | |
|---|---|---|---|
| | | *E. coli* ATCC 11229 | *S. aureus* ATCC 6538 |
| HPMC (10% glycerin) + EtOH | Brand A | 3.0 | 5.0 |
| | Brand B | 3.6 | 2.9 |
| | Brand C | 2.3 | 2.7 |
| HPMC (5% glycerin) + EtOH | Brand A | 2.6 | 4.6 |
| | Brand B | 3.2 | 2.5 |
| | Brand C | 2.0 | 2.3 |

Example 3

TABLE 5

Anti-adherent agents in alcohol formulations using the Viable Count Anti-Adherence Test Method.

| Agent 1 | Con. Wt. % | Agent 2 | Con. Wt. % | Ethanol (w/w %) | Glycerin (%) | Water (%) | Average LOG reduction *E. coli* ATCC** 11229 | Average LOG reduction *S. aureus* ATCC** 6538 |
|---|---|---|---|---|---|---|---|---|
| ACULYN 22 pH 6.5 | 2 | | | 60 | 5 | QS | 1.7 | 1.3 |

TABLE 5-continued

Anti-adherent agents in alcohol formulations using the Viable Count Anti-Adherence Test Method.

| Agent 1 | Con. Wt. % | Agent 2 | Con. Wt. % | Ethanol (w/w %) | Glycerin (%) | Water (%) | Average LOG reduction E. coli ATCC** 11229 | Average LOG reduction S. aureus ATCC** 6538 |
|---|---|---|---|---|---|---|---|---|
| ACULYN 22 pH 6.5 | 2 | ARISTO-FLEX VELVET | 0.4 | 60 | 5 | QS | 1.7 | 0.99 |
| CMC pH 5 | 2 | | | 60 | 5 | QS | 1.91 | 1.31 |
| Gum Arabic | 4 | | | 60 | 5 | QS | 0.85 | 1.20 |
| PECOGEL GC-310 | 5 | | | 60 | 5 | QS | 1.16 | 1.21 |
| PECOGEL H-12 | 5 | | | 60 | 5 | QS | 1.47 | 0.77 |
| SESAFLASH | 5 | ARISTO-FLEX VELVET | 0.4 | 60 | 5 | QS | 1.20 | 0.54 |
| ACULYN 38 | 1 | | | 60 | 5 | QS | 0.62 | 0.67 |
| BENECEL A4C | 1 | | | 60 | 5 | QS | 1.83 | 1.68 |
| BENECEL A4C | 1 | ARISTO-FLEX VELVET | 0.4 | 60 | 5 | QS | 2.01 | 2.59 |
| BENECEL E15 | 0.5 | ARISTO-FLEX VELVET | 0.4 | 60 | 5 | QS | 1.40 | 1.52 |
| BENECEL E15 | 0.5 | | 0.4 | 60 | 5 | QS | 1.89 | 1.50 |
| BENECEL K100LV | 1 | ARISTO-FLEX VELVET | | 60 | 5 | QS | 1.21 | 1.15 |
| KLUCEL ECS | 0.6 | | | 60 | 5 | QS | 0.66 | 1.08 |
| PROTANAL ESTER BV-3750 | 4 | | | 60 | 5 | QS | 0.99 | 0.65 |
| NATROSOL 250 LR | 1 | | | 60 | 5 | QS | 1.08 | 1.02 |
| SEPIMAX ZEN | 0.4 | | | 60 | 5 | QS | 0.51 | 0.70 |

Multiple compositions were prepared with varying combinations of anti-adherent agents, labeled Agent 1 and Agent 2, as displayed in Table 5. As can be seen in the table, Agent 1 materials were added and mixed into a constant quantity of Ethanol and Glycerin with the remaining balance of each composition consisting of water to a total of 100% w/w. Additionally, for some of the compositions, a second anti-adherent agent, Agent 2, was added to the compositions. For these compositions, Agent 1 and Agent 2 were mixed into a constant quantity of Ethanol and Glycerin with the remaining balance consisting of water to a total of 100% w/w. All of the compositions in Table 6 were then tested for anti-adherence against Gram− and Gram+ microbes using the Viable Count Anti-Adherence Test Method. As can be seen in Table 5, all of the compositions containing Agent 1 or a combination of Agent 1 and Agent 2 reduced the adherence of microbes on the surface by at least 0.5 LOG according to the Viable Count Anti-Adherence Test Method.

Test Methods

High Throughput Anti-Adherence Test Method

This test method specifies the operational parameters required to grow and or prevent the formation of bacterial attachment using a high throughput screening assay. The assay device consists of a plastic lid with ninety-six (96) pegs and a corresponding receiver plate with ninety-six (96) individual wells that have a maximum 200 μL working volume. Biofilm is established on the pegs under static batch conditions (i.e., no flow of nutrients into or out of an individual well).

1. Terminology
   1.2 Definitions of Terms Specific to This Standard:
       1.2.2 peg, n—biofilm sample surface (base: 5.0 mm, height: 13.1 mm).
       1.2.3 peg lid, n—an 86×128 mm plastic surface consisting of ninety-six (96) identical pegs.
       1.2.4 plate, n—an 86×128 mm standard plate consisting of ninety-six (96) identical wells.
       1.2.5 well, n—small reservoir with a 50 to 200 μL working volume capacity.
2. Acronyms
   2.2 ATCC: American Type Culture Collection
   2.3 CFU: colony forming unit
   2.4 rpm: revolutions per minute
   2.5 SC: sterility control
   2.6 TSA: tryptic soy agar
   2.7 TSB: tryptic soy broth
   2.8 GC: growth control
3. Apparatus
   3.2 Inoculating loop—nichrome wire or disposable plastic.

3.3 Petri dish—large labelled (100×150×15 mm, plastic, sterile) for plating.
3.4 Microcentrifuge tubes—sterile, any with a 1.5 mL volume capacity.
3.5 96-well microtiter plate—sterile, 86×128 mm standard plate consisting of ninety-six (96) identical flat bottom wells with a 200 μL working volume.
3.6 Vortex—any vortex that will ensure proper agitation and mixing of microfuge tubes.
3.7 Pipette—continuously adjustable pipette with volume capability of 1 mL.
3.8 Micropipette—continuously adjustable pipette with working volume of 10 μL±200 μL.
3.9 Sterile pipette tips-200 uL and 1000 uL volumes.
3.10 Sterile reagent reservoir-50 mL polystyrene.
3.11 Sterilizer—any steam sterilizer capable of producing the conditions of sterilization.
3.12 Colony counter—any one of several types may be used. A hand tally for the recording of the bacterial count is recommended if manual counting is done.
3.13 Environmental incubator—capable of maintaining a temperature of 35±2° C. and relative humidity between 35 and 85%.
3.14 Reactor components—the MBEC Assay device, available from Innovotech, Edmonton, AB, Canada.
3.15 Sterile conical tubes—50 mL, used to prepare initial inoculum.
3.16 Appropriate glassware—as required to make media and agar plates.
3.17 Erlenmeyer flask—used for growing broth inoculum.
3.18 Positive Displacement pipettes capable of pipetting 200 μL.
3.19 Sterile pipette tips appropriate for Positive Displacement pipettes.
4. Reagents and Materials
    4.2 Purity of water—all references to water as diluent or reagent shall mean distilled water or water of equal purity.
    4.3 Culture media:
    4.4 Bacterial growth broth—Tryptic soy broth (TSB) prepared according to manufacturer's directions.
    4.5 Bacterial plating medium—Tryptic soy agar (TSA) prepared according to manufacturer's directions.
    4.6 Phosphate Buffered Saline (PBS)—
    4.7 Rinse Solution: Sterile PBS and TWEEN 80 (Sigma-Aldrich, St. Louis, Mo.) 1% w/v.
5. Microorganisms
    5.1 $E.\ coli$ ATCC 11229 and $S.\ aureus$ ATCC 6538
6 Test Method Overview: The experimental process for the High-Throughput Anti-Adherence Test Method. This standard protocol may be broken into a series of small steps, each of which is detailed in the sections below.
    6.1 Culture Preparation
        6.1.1 $E.\ coli$ ATCC 11229 and $S.\ aureus$ ATCC 6538 are the organisms used in this test.
        6.1.2 Using a cryogenic stock (at −70° C.), streak out a subculture of the above listed microorganisms on organism's specific agar (TSA).
        6.1.3 Incubate at 35±2° C. for the period of time of 22±2 hours.
        6.1.4 Aseptically remove isolated colony from streak plate and inoculate 20 mL of sterile TSB.
        6.1.5 Incubate flask at 35±2° C. and 175±10 rpm for 16 to 18 hours ($E.\ coli$ and $S.\ aureus$). Viable bacterial density should be $10^9$ CFU/mL and should be checked by serial dilution and plating.
        6.1.6 Pipette 10 mL from the incubation flask of $E.\ coli$, and $S.\ aureus$ into a 50 mL conical tube and spin down at 5 minutes at 4,000×g. Then remove supernatant and Resuspend in 10 mL sterile PBS. Approximate cell density should be $10^7$-$10^9$ CFU/mL. Vortex the sample for approximately 30 seconds to achieve a homogeneous distribution of cells.
        6.1.7 Perform 10-fold serial dilutions of the inoculum in triplicate.
        6.1.8 Plate appropriate dilutions on appropriately labelled TSA plates. Incubate the plates at 35±2° C. for 22±2 hours depending on the isolates growth rate and enumerate.
    6.2 Preparation of the Challenge plates:
        6.2.1 Preparation of agents and coating agents onto MBEC plate lid
            6.2.1.1.1 Using a positive displacement pipette aseptically add 200 μL of agents and control to be tested to a sterile 96-well microplate according to the plate layout of Table 6.

TABLE 6

Sample layout of 96-well MBEC plate.

| | | 1 | 2 | 3 | 4 | 5 | 6 | 7 | 8 | 9 | 10 | 11 | 12 |
|---|---|---|---|---|---|---|---|---|---|---|---|---|---|
| E. coli | A | AAC | | T1 | T2 | T3 | T4 | T5 | T6 | T7 | T8 | NT-GC | T1-SC |
| E. coli | B | AAC | | T1 | T2 | T3 | T4 | T5 | T6 | T7 | T8 | NT-GC | T2-SC |
| E. coli | C | AAC | | T1 | T2 | T3 | T4 | T5 | T6 | T7 | T8 | NT-GC | T3-SC |
| E. coli | D | AAC | | T1 | T2 | T3 | T4 | T5 | T6 | T7 | T8 | NT-GC | T4-SC |
| S. aureus | E | AAC | | T1 | T2 | T3 | T4 | T5 | T6 | T7 | T8 | NT-GC | T5-SC |
| S. aureus | F | AAC | | T1 | T2 | T3 | T4 | T5 | T6 | T7 | T8 | NT-GC | T6-SC |
| S. aureus | G | AAC | | T1 | T2 | T3 | T4 | T5 | T6 | T7 | T8 | NT-GC | T7-SC |
| S. aureus | H | AAC | | T1 | T2 | T3 | T4 | T5 | T6 | T7 | T8 | NT-GC | T8-SC |

AAC = Anti-Adherent Control
NT-GC = No Treatment Growth Control
SC = Sterility Control
T1-T8 = Test Codes 6.2.1.1.2 Add 200 µL of each code to the appropriate well for sterility controls.

6.2.1.1.3 Place the MBEC plate lid, peg side down into the 96-well microplate containing the test compound solutions.

6.2.1.1.4 Allow the plate to sit at room temperature (25±3° C.) for 2 hours.

6.2.1.1.5 Remove the MBEC plate lid and allow the lid to dry at room temperature (25±3° C.) overnight in a laminar flow hood.

7.1 Bacterial Adherence Challenge:
   7.1.1 Add 100 µL of diluted bacteria to the appropriate wells in a sterile 96-well microplate as indicated in the plate layout in Table 6.
   7.1.2 Add 200 µL of sterile PBS to the sterility controls.
   7.1.3 The MBEC containing dried agents is then inserted into the bacterial inoculated 96 well flat bottom microplate from section 9.3.1
   7.1.4 Incubate stationary at room temperature (25±3° C.) for 15 minutes.
   7.1.5 Remove the MBEC lid and place into a 96-well microplate containing 200 µL PBS+1% w/v TWEEN 80. Incubate stationary at room temperature (25±3° C.) for 15 seconds.
   7.1.6 Repeat step 7.1.5 for two additional washes for a total of 3 washes.

7.2 Method to Determine Number of Attached Bacteria
   7.2.1 Transfer the washed MBEC plate lid to a 96-well plate containing 200 µL ALAMARBLUE reagent (prepared according to manufacturer's directions, Life Technologies, Carlsbad, Calif.) in each well to be tested.
   7.2.2 The final plate is transferred to a SPECTRAMAX GEMINI EM microplate reader (Molecular Devices, Inc. Sunnyvale, Calif. USA) for a 20 hour kinetic, bottom read with an excitation of 560 nm and emission of 590 nm. The rate of fluorescence development (relative fluorescence units (RFU)/minute) is determined for each well.
   7.2.3 Data was analyzed using a standard curve (described below) for each organism to determine the numbers of bacteria attached to the pegs (LOG CFU/mL) present in each sample. Number of attached bacteria was quantified by incubating with an ALAMARBLUE reagent and measuring fluorescence development over time.
   7.2.4 From these data, the LOG CFU/mL reduction of each time point relative to the growth control is calculated to determine the activity of each code.

7.3 Method for Generating a Standard Curve with bacteria in an ALAMARBLUE Solution:
   7.3.1 Standard curves were constructed for each organism to define the rate of fluorescence development as a function of bacterial concentration, as determined via viable plate counts. This standard curve provided the ability to relate rate of fluorescence development (RFU/minute) to the LOG CFU/mL number of bacteria present in a given sample
   7.3.2 Day 1:
      7.3.2.1 Aseptically remove loopful of bacteria strain to be tested from freezer stock and place in 20 mL of TSB media in a culture flask.
      7.3.2.2 Incubate with shaking (200 rpm) for 22±2 hours at 37±2° C.
   7.3.3 Day 2:
      7.3.3.1 Aseptically transfer 100 µL of the 22±2 hours freezer stock cultures into 20 mL of TSB media in a culture flask.
      7.3.3.2 Incubate cultures on a gyrorotary shaker (200 rpm) for 22±2 hours at 37±2° C.
      7.3.3.3 Perform a streak for isolation from the culture flask on TSA. Incubate plate for 22±2 hours at 37±2° C.
   7.3.4 Day 3:
      7.3.4.1 Prepare an ALAMARBLUE solution according to the manufacturer's directions.
      7.3.4.2 Remove culture flask from shaking incubator after 22±2 hours. Pipette 1 mL of bacteria into a 1.7 mL microcentrifuge tube.
      7.3.4.3 Centrifuge the bacteria at 4000×g.
      7.3.4.4 Resuspend bacterial cells in sterile PBS. Perform a total of two washes.
      7.3.4.5 Perform 1:10 serial dilutions with washed bacterial culture in 0.9 mL dilution blanks of sterile PBS (100 µL culture into 900 µL of sterile PBS).
      7.3.4.6 Plate appropriate dilutions of prepared bacteria.
      7.3.4.7 Add 270 µL of ALAMARBLUE solution to wells A-D: columns 1-7 of a 96-well plate.
      7.3.4.8 Add 30 µL of bacterial dilution the wells of a 96-well plate (n=4 per dilution).
      7.3.4.9 Add 30 µL of sterile PBS to wells A-D, column 8 for a background control.
      7.3.4.10 Place plate in a bottom reading spectrophotometer that measures fluorescence. Set temp to 37° C. Perform assay at 37° C., read every 20 minutes for 24 hours at 560 excite and 590 emit.
      7.3.4.11 Enumerate the dilutions.
      7.3.4.12 Calculate the mean rate of fluorescence development.
      7.3.4.13 Plot the mean rate of fluorescence development as a function of the mean CFU/mL of the dilutions.

Viable Count Anti-Adherence Test Method

This test method specifies the operational parameters required to grow and or prevent the formation of bacterial attachment using viable counts. The assay device consists of a plastic lid with ninety-six (96) pegs and a corresponding receiver plate with ninety-six (96) individual wells that have a maximum 200 µL working volume. Biofilm is established on the pegs under static batch conditions (i.e., no flow of nutrients into or out of an individual well).

This test method is identical to the High Throughput Anti-Adherence Test Method except that Section 7.1 through 7.3.4.13 is replaced with the following:

A. Bacterial Adherence Challenge:
   A.1 Add 100 µL of diluted bacteria to the appropriate wells in a sterile 96-well microplate as indicated in the plate layout in Table 4.
   A.2 Add 200 µL of sterile PBS to the sterility controls.
   A.3 The MBEC containing dried agents is then inserted into the bacterial inoculated 96 well flat bottom microplate from section 9.3.1

B. Recovery:
   B.1 After the 15 minute contact time, transfer the MBEC™ lid to the rinse plate where each well contains 200 µL for 15 seconds of saline and 1% Tween 80 to wash of any loosely attached planktonic cells. Repeat this for 3 separate wash plates.

B.2 *S. aureus* Recovery:
- B.2.1 Break the corresponding pegs from the MBEC™ lid using a sterile pliers and transfer them into 50 mL conical tubes containing 10 mL PBS.
- B.2.2 Vortex the conical tubes for 10 seconds
- B.2.3 Transfer the conical tubes to the sonicator and sonicate on high. Sonicate for 1 minute on. Then allow the tubes to rest for 1 minute. Repeat the sonication step for a total of 5 minutes of sonication to dislodge surviving attached bacteria. The conical tubes were placed in the sonicator water bath using a float.
- B.2.4 Vortex the conical tubes again for 10 seconds.

B.3 *E. coli* Recovery:
- B.3.1 Transfer the MBEC™ lid to a plate containing 200 μL PBS.
- B.3.2 Transfer the plate to the sonicator and sonicate on high for 10 minutes to dislodge surviving attached bacteria. The plates are placed in a dry stainless steel insert tray which sits in the water of the sonicator. The vibrations created in the water by the sonicator transfer through the insert tray to actively sonicate the contents of the 96 well recovery plate(s).

C. $LOG_{10}$ Reduction:
- C.1 Following sonication, place 100 μL from each well of the MBEC™ plate, into the first 12 empty wells of the first row of a 96 well-micro titer plate. Place 180 μL of sterile 0.9% saline in the remaining rows.
- C.2 Prepare a serial dilution ($10^0$-$10^{-7}$ by moving 20 μL down each of the 8 rows.
- C.3 Remove 10 μL from each well and spot plate on a prepared TSA plates.
- C.4 Plates are incubated at 37±1° C. and counted after approximately 24 h hours of incubation.
- C.5 Data will be evaluated as Log 10 CFU/peg.
- C.6 Cell Enumeration:
- C.7 Count the appropriate number of colonies according to the plating method used.
- C.8 Calculate the arithmetic mean of the colonies counted on the plates.
  - C.8.1 The log density for one peg is calculated as follows:

$Log_{10}(CFU/peg)=Log_{10}[(X/B)(D)]$ where:

X=mean CFU; 8=volume plated (0.02 mL); and D=dilution.

- C.9 Calculate the overall attached bacteria accumulation by calculating the mean of the log densities calculated.
- C.10 Calculate the $Log_{10}$ reduction for each dilution as follows: $LOG_{10}$ Reduction=Mean $LOG_{10}$ Growth Control−Mean $Log_{10}$ Test.

Explanation of Log Decrease

The compositions of the present disclosure exhibit a decrease of bacteria on surfaces. Log decrease, for example, may be determined from the decrease of bacteria adhered to a surface according to the following correlations:

| Fold Decrease of Bacteria | LOG Decrease |
| --- | --- |
| 1 | 0.5 |
| 10 | 1 |
| 100 | 2 |
| 1000 | 3 |

In other words, surface exhibiting a decrease of bacteria of 1 Log means the number of bacteria on the fibrous substrate has decreased 10-fold, a decrease of 2 Log means the number of bacteria has decreased 100-fold, a decrease of 3 Log means the number of bacteria has decreased 1000-fold, etc., as compared to the number of bacteria present on a surface that is not treated with the disclosed composition. A larger Log decrease thus corresponds with a composition that is able to more effectively repel Gram negative and Gram positive bacteria.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. A anti-adherent composition for use on surfaces, the composition comprising:
   at least 60% (by weight of composition) of a short-chain alcohol; and
   an anti-adherent agent selected from the group consisting of Acacia Senegal Gum; Polyacrylate Crosspolymer-11; VP/Dimethylaminoethylmethacrylate/Polycarbamyl Polyglycol Ester; Acrylates/Vinyl Neodecanoate Crosspolymer; Propylene Glycol Alginate; Polyacrylate Crosspolymer-6; VP/Polycarbamyl Polyglycol Ester; and combinations thereof.

2. The composition of claim 1 wherein the anti-adherent agent comprises Polyacrylate Crosspolymer-11.

3. The composition of claim 1 wherein the anti-adherent agent comprises Polyacrylate Crosspolymer-11, and wherein the composition further includes Hydroxypropyl methylcellulose (HPMC), and wherein the weight/weight ratio of HPMC to Polyacrylate Crosspolymer-11 ranges from 10:1 to 1:10, respectively.

4. The composition of claim 1 wherein the anti-adherent agent is present in the amount of 0. 01% to 20% by weight of the composition.

5. The composition of claim 1 wherein composition reduces the adherence of microbes on the surface by at least 0.5 LOG according to the High Throughput Anti-adherence Test Method or the Viable Count Anti-Adherence Test Method.

6. The composition of claim 1 wherein composition reduces the adherence of microbes on the surface by at least 1 LOG according to the High Throughput Anti-adherence Test Method or the Viable Count Anti-Adherence Test Method.

7. The composition of claim 1 further comprising a hydrophilic carrier.

8. The composition of claim 1 further comprising a humectant selected from the group consisting of glycerin, glycerin derivatives, hyaluronic acid derivatives, betaine derivatives amino acids, amino acid derivatives, glycosaminoglycans, glycols, polyols, sugars, sugar alcohols, hydrogenated starch hydrolysates, hydroxy acids, hydroxy acid derivatives, salts of PCA, and combinations thereof.

9. The composition of claim 1 further comprising a humectant selected from the group consisting of honey, sorbitol, hyaluronic acid, sodium hyaluronate, betaine, lactic acid, citric acid, sodium citrate, glycolic acid, sodium glycolate ,sodium lactate, urea, propylene glycol, butylene glycol, pentylene glycol, ethoxydiglycol, methyl gluceth-10, methyl gluceth-20, PEG-2, PEG-3, PEG-4, PEG- 5, PEG-6, PEG-7, PEG-8, PEG-9, PEG 10, Propanediol, xylitol, maltitol, and a combination thereof.

10. The composition of claim 1 further comprising a foaming agent.

11. A wipe comprising:
   a nonwoven substrate; and
   an anti-adherent composition comprising at least 60% (by total weight of composition) of a short-chain alcohol; an anti-adherent agent, wherein the anti-adherent agent comprises Acacia Senegal Gum; Polyacrylate Crosspolymer-11; VP/Dimethylaminoethylmethacrylate/Polycarbamyl Polyglycol Ester; Acrylates/Vinyl Neodecanoate Crosspolymer; Propylene Glycol Alginate; Polyacrylate Crosspolymer-6; VP/Polycarbamyl Polyglycol Ester; and combinations thereof.

12. The wipe of claim 11, wherein the composition further comprises a hydrophilic carrier.

13. The wipe of claim 11, wherein the anti-adherent agent is present in the amount of 0.01% to 20% (by total weight of composition).

14. The wipe of claim 11, wherein the anti-adherent agent is present in the amount of 0.01% to 10% (by total weight of composition).

15. The wipe of claim 11, wherein the composition further comprises a humectant.

16. The wipe of claim 15, wherein the humectant is selected from the group consisting of glycerin, glycerin derivatives, hyaluronic acid derivatives, betaine derivatives amino acids, amino acid derivatives, glycosaminoglycans, glycols, polyols, sugars, sugar alcohols, hydrogenated starch hydrolysates, hydroxy acids, hydroxy acid derivatives, salts of PCA, and combinations thereof.

17. The wipe of claim 15, wherein the humectant is selected from the group consisting of honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, PEG-2, PEG-3, PEG-4, PEG-5, PEG-6, PEG-7, PEG-8, PEG-9, PEG 10, Propanediol, xylitol, maltitol, and a combination thereof.

18. The wipe of claim 11, wherein the composition reduces the adherence of microbes on the surface by at least 0.5 LOG according to the High Throughput Anti-adherence Test Method or the Viable Count Anti-Adherence Test Method.

19. The wipe of claim 11, wherein the composition reduces the adherence of microbes on the surface by at least 1.0 LOG according to the High Throughput Anti-adherence Test Method or the Viable Count Anti-Adherence Test Method.

20. A method of reducing adherence of microbes to a surface, the method comprising:
   providing the anti-adherent composition of claim 1; and
   applying the anti-adherent composition to the surface.

* * * * *